(12) United States Patent
Chih-hui

(10) Patent No.: US 6,723,371 B2
(45) Date of Patent: Apr. 20, 2004

(54) PROCESS FOR PREPARING AN ELECTROCHEMICAL TEST STRIP

(75) Inventor: Lee Chih-hui, Kaohsiung (TW)

(73) Assignee: Bioptik Technology, Inc., Hsinchu (TW)

( * ) Notice: Subject to any disclaimer, the term of this patent is extended or adjusted under 35 U.S.C. 154(b) by 29 days.

(21) Appl. No.: 09/871,350

(22) Filed: May 31, 2001

(65) Prior Publication Data

US 2002/0003087 A1 Jan. 10, 2002

(30) Foreign Application Priority Data

Jun. 1, 2000  (TW) .......................................... 89110763

(51) Int. Cl.[7] .......................... B05D 3/00; G01N 27/327
(52) U.S. Cl. ................................. 427/2.13; 204/403.01
(58) Field of Search ....................... 204/403.01, 403.14, 204/403.06, 403.09; 427/2.13

(56) References Cited

U.S. PATENT DOCUMENTS

| 4,886,740 A | * | 12/1989 | Vadgama | .................... 205/778 |
| 5,658,443 A | * | 8/1997 | Yamamoto et al. | .... 204/403.08 |
| 5,727,548 A | * | 3/1998 | Hill et al. | ................... 600/372 |
| 6,054,039 A | * | 4/2000 | Shieh | .......................... 205/778 |
| 6,063,259 A | * | 5/2000 | Wang et al. | .............. 205/777.5 |

FOREIGN PATENT DOCUMENTS

JP   01134246 a   *  5/1989

OTHER PUBLICATIONS

JPO abstract of Kawaguri et al. (JP 01–134246 A).*

* cited by examiner

*Primary Examiner*—T. Tung
*Assistant Examiner*—Alex Noguerola
(74) *Attorney, Agent, or Firm*—Jiawei Huang; J.C. Patents

(57) ABSTRACT

As embodied and broadly described herein, the invention provides an electrode test strip. The electrochemical electrode test strip comprises an insulating base plate, a electrode system on the base plate, a spacer which partially covers the electrode system and a channel trench with a constant width is formed thereof, a reactive film, and a cover on the spacer with an first opening thereof. Wherein the electrode system comprises at least a working electrode and a reference electrode, and the working electrode and the reference electrode is isolated. The reactive film contains at least on active species that can have a specific redox reaction with the analyte. The first opening exposes the channel trench, and two second openings are located at the two ends of the channel trench.

11 Claims, 7 Drawing Sheets

PROCESS FOR PREPARING AN ELECTROCHEMICAL TEST STRIP

CROSS-REFERENCES TO THE RELATED APPLICATIONS

This application claims the priority benefit of Taiwan application serial no. 89110763, filed Jun. 1, 2000, the full disclosure of which is incorporated herein by reference.

BACKGROUND OF THE INVENTION

1. Field of Invention

The present invention relates to an electrochemical electrode test strip and a process for preparation thereof. More particularly, the present invention relates to an electrochemical electrode test strip that utilizes a reactive film that contains an active species that can undergo redox reactions to contact with a sample, than a specific biochemical or chemical redox reaction occurs to transfer electrons between the active species and the an analyte of the sample. The electrochemical electrode test strip needs only low sample amount, and it is disposable.

2. Description of Related Art

Electrode test strips are not a new technology. In present market, electrode test strips are applied to produce various blood glucose test strips that can be used in home. But there still are some problems of the reactive region design for a test strip. Therefore, the sample adding method and the sample volume needed often introduce contamination and insufficient sample volume, and hence measurement errors are produced. For example, the time needed to introduce sample for fulfilling the reactive region is too long to give rise to reaction time delay. Or fingertips touch the reactive region to containment the test strip; therefore the test result errors are produced. Especially, when the lancet is used to gather blood from the babies and the olds, the blood volume is hard to reach the optimum volume, and test errors are occurred. Hence, a test strip that needs only minimal sample volume is required. Below 5 $\mu$L sample volume is preferred for a siphonal test strip.

In FIG. 1, a perspective view of a commercialized blood-glucose electrode test strip is shown (U.S. Pat. No. 5,120,420). This test strip includes an insulating base plate 101, and a two-electrode system 102 is formed thereon. A second insulating layer 105 covers the insulating base plate 101, wherein an U-type opening 103 exposes one end of the two electrodes 102 surface and opening 104 exposes the other end of the two electrode 102 surface. Electrodes exposed by opening 103 serve as cathode lead and anode lead respectively. The opening 104 serves to define a reactive region over the electrodes 102. A reagent covers the reactive region. After the reagent is dried, the mesh 106 completely covers the reactive region. An adhesive tape 107 with a hole 110 attaches to the upper surface of the mesh 106 to fix mesh 106 and protect the reactive region. The hole 110 serves as a sample inlet. Two slits 108 and 109 that lay beside the mesh 105 are used to discharge gas.

However, this type of test strip can only reduce the sample volume requirement down to 9 $\mu$L. Besides, the gas discharging effect of the two slits 108 and 109 is poor.

In FIG. 2, a perspective view of another commercialized blood-glucose electrode test strip is shown (U.S. Pat. No. 5,120,420). This test strip includes a base plate 201, and leads 202, a working electrode 204, a reference electrode 205, a spacer 206 and a cover 210 are formed thereon. The central part of the spacer 206 is cut off to form a U-shaped space 207, which forms a sample loading space i.e. a reactive region. The space 207 has a sample inlet 208 and a gas outlet 209.

The forming method of a reactive film (not shown in FIG. 2) of the blood-glucose electrode test strip includes steps as follows. Leads 202 are covered by a carboxymethyl cellulose (CMC) aqueous solution, then the CMC aqueous solution is dried to form a hydrophilic CMC layer. A glucose oxidase (GOD) solution is spread and dried to form a GOD layer thereon. A hydrophilic PVP polymer solution is spread and dried to form a PVP layer thereon. Finally, an electron medium suspension solution is spread and dried thereon to form an electron medium layer. The CMC layer, the GOD layer, the PVP layer and the electron medium layer compose the reactive film on the reactive region.

The reactive layer described above is composed of four layers (a CMC layer, a GOD layer, a PVP layer and an electron medium layer), and a drying step is performed after solution of each layer described above is formed. Hence the procedure of producing the reactive layer is very complicate. Besides, the time for a sample fulfill the space 207 to initiate the electrodes 204 and 205 working needs a certain period of time, which results in a measurement delay and thus measurement errors are produced.

SUMMARY OF THE INVENTION

The invention provides an electrochemical electrode test strip that has three sample inlets. A sample can be introduced from one of the three inlets, and the other two inlets can serve as gas outlets. The design of the electrochemical electrode test strip can provide a more convenient way to operate it.

The invention provides a different electrochemical electrode test strip, which has a sample inlet and two gas outlets. The time needed for the sample to fulfill the reactive space is shortened to reduce the detecting errors.

The invention provides an electrochemical electrode test strip that the sample volume needed is less than 5 $\mu$L.

The invention provides an electrochemical electrode test strip that the sample volume needed is fixed to minimize the detecting errors caused by different sample volume.

The invention provides an easy method to produce an electrochemical electrode test strip. This method simplifies the producing process of a reactive film to shorten the time needed for mass-producing the electrochemical electrode test strip.

As embodied and broadly described herein, the invention provides an electrode test strip. The electrochemical electrode test strip comprises an insulating base plate, a electrode system on the base plate, a spacer which partially covers the electrode system and a channel trench with a constant width is formed thereof, a reactive film, and a cover on the spacer with an first opening thereof. Wherein the electrode system comprises at least a working electrode and a reference electrode, and the working electrode and the reference electrode is isolated. The reactive film contains at least one active species that can have a specific redox reaction with the analyte. The first opening exposes the channel trench, and two second openings are located at the two ends of the channel trench.

This invention also provides a method of manufacturing an electrode test strip, comprising the following steps. An insulating base plate is offered first. Than a layer of conductive films to be a cathode and an anode is printed on the insulating base plate, and the cathode and the anode are isolated. A first spacer and a second spacer on the conductive films is formed to expose two ends of the cathode and the anode, wherein a channel trench is formed between the first and the second spacer. A reagent solution is spread on a bottom surface of the channel trench, and then the reagent solution is dried to form a reactive film in the channel trench. The reagent solution contains an active species, a polymer, an electron medium, a nonionic surfactant and a buffer solution. A cover with a first opening is formed on the spacer, wherein the first opening is located on the channel trench and two second openings are surrounded by the insulating base plate, the first spacer, the second spacer and the cover.

According to the present invention, a sample can be loaded from one of the first and second openings into the reactive region of the electrochemical electrode test strip. Therefore, the sample can be easily loaded into the reactive region in a much shorter time and the sample can easily cover the reactive film completely, and thus larger redox current can be produced which can largely reduce the measure errors. Besides the reagent solution can be spread on the reactive region and dried in one time. This will safe much time and cost needed for manufacturing the electrode test strip.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE PREFERRED EMBODIMENTS

I. The structure of a Electrochemical Electrode Test Strip of This Invention

Figure 1:
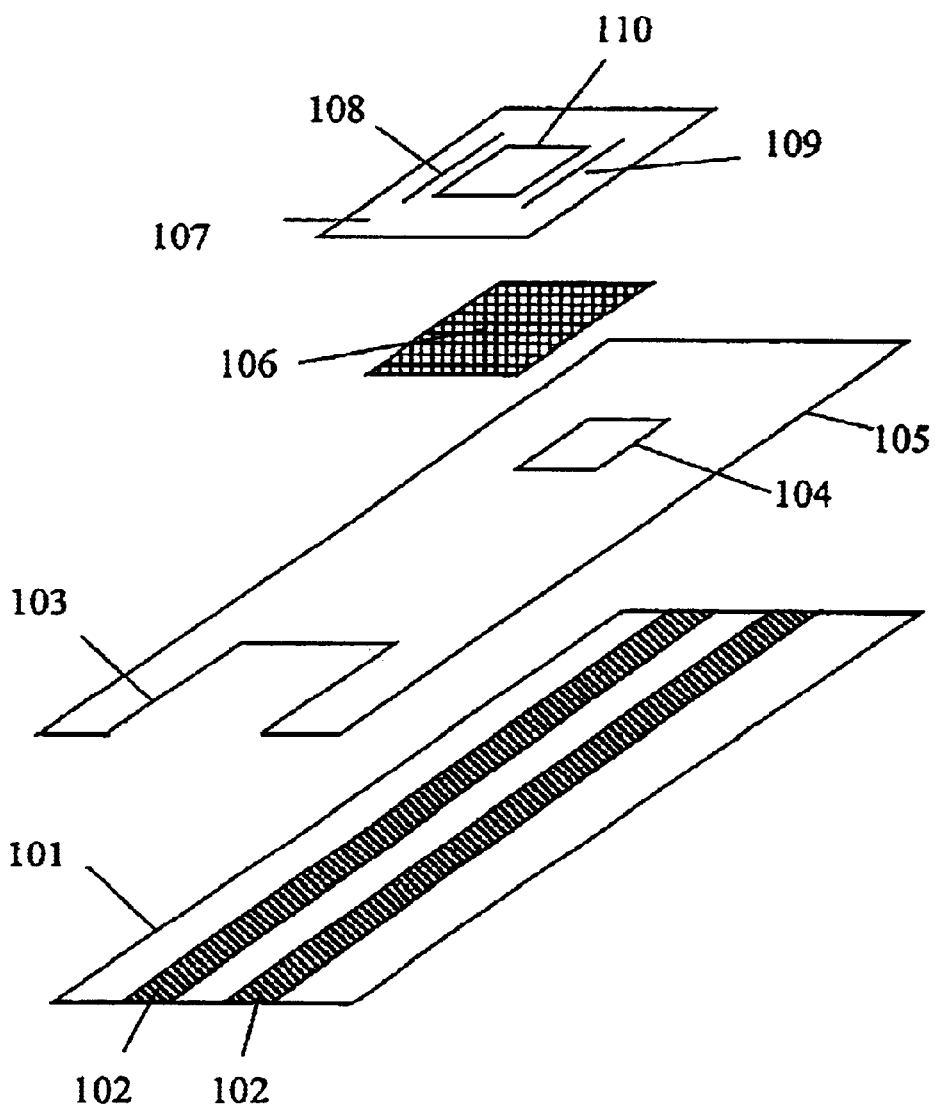
FIG. 1 is a perspective view of a commercialized blood-glucose electrode test strip.
Figure 2:
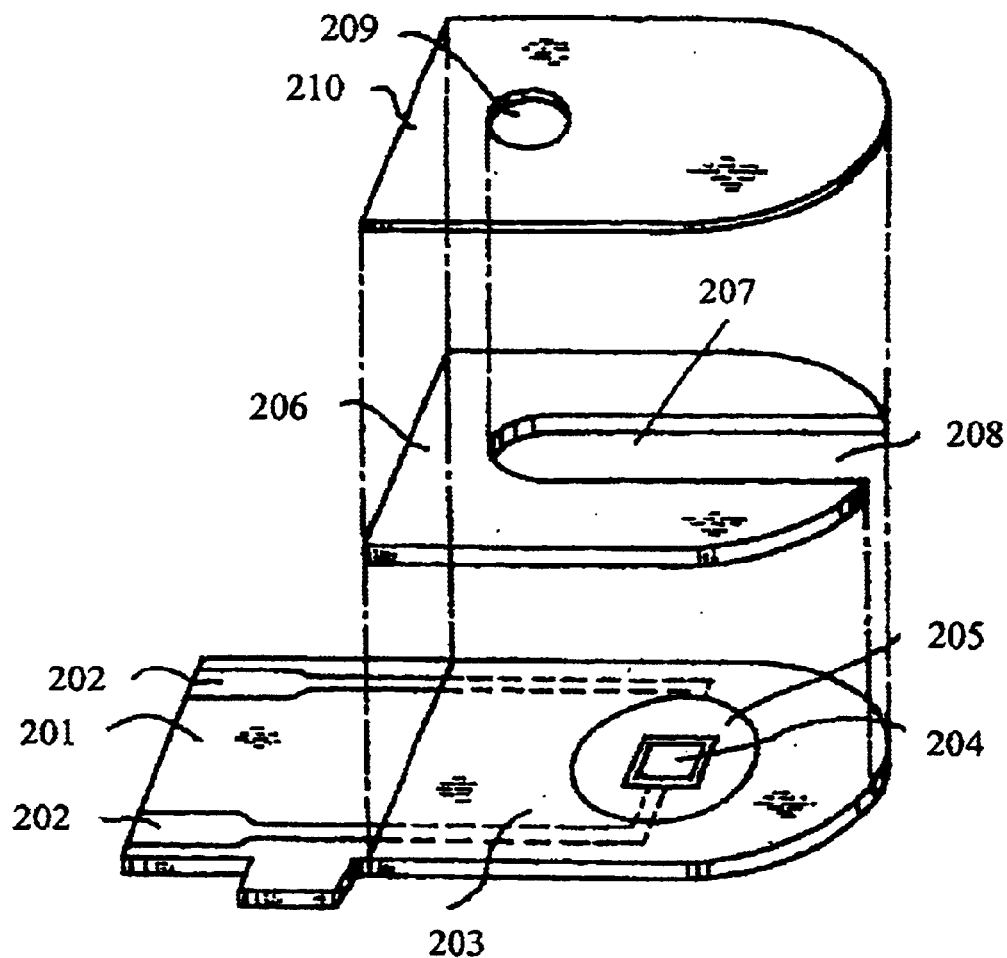
FIG. 2 is a perspective view of another commercialized blood-glucose electrode test strip.
Figure 3A:
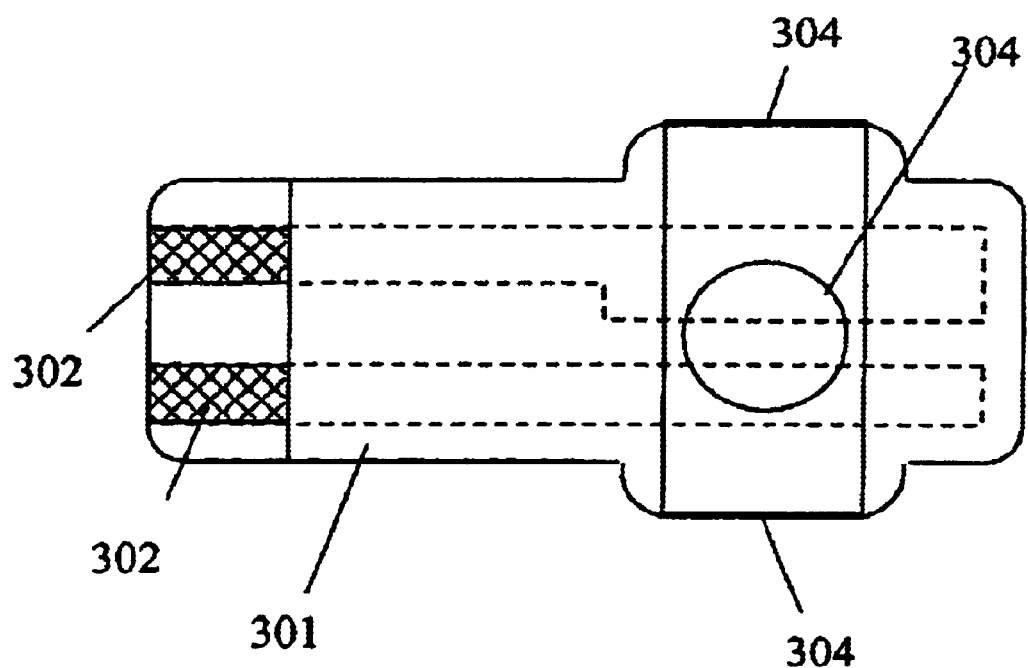
FIG. 3A is a top view of a electrode test strip according to one preferred embodiment of this invention.
Figure 3B:
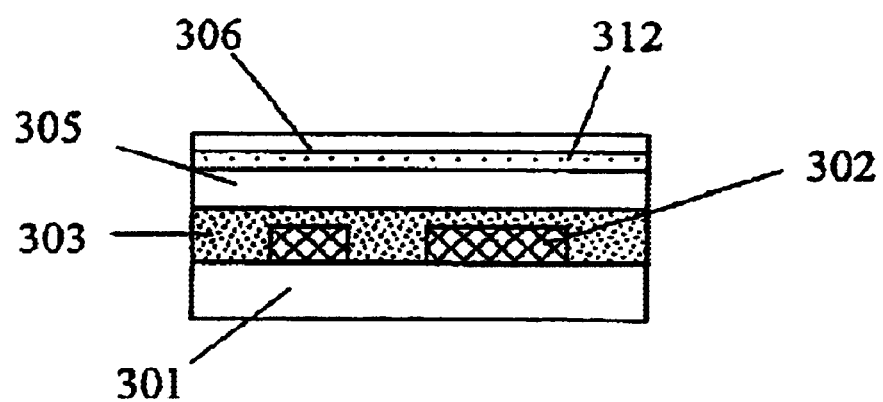
FIG. 3B is a front view of the above electrode test strip according to one preferred embodiment of this invention.
Figure 3C:
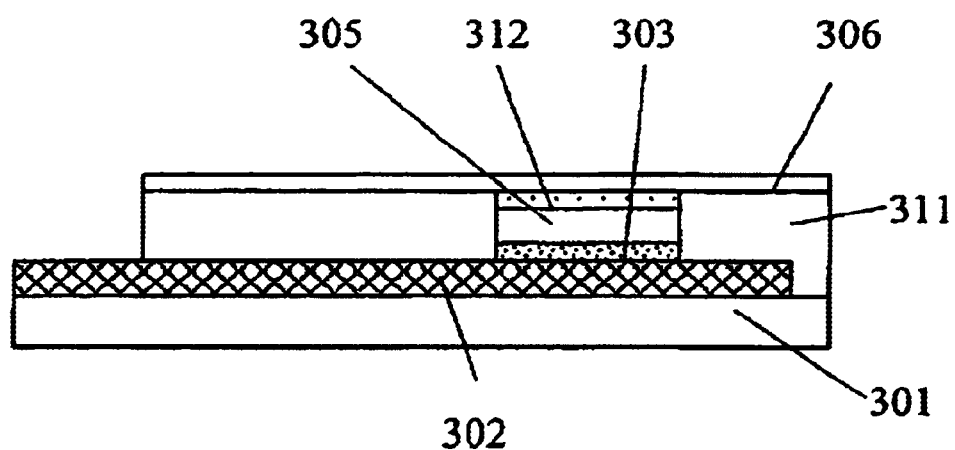
FIG. 3C is a side view of the above electrode test strip according to one preferred embodiment of this invention.

The appearance of an electrochemical electrode test strip according to one preferred embodiment of this invention are individually shown in FIGS. 3A–3C. FIGS. 3A–3C individually show the top view, the front view and the side view of the electrochemical electrode test strip. The structure of the electrochemical electrode test strip comprises a base plate 301, conductive films 302 on the base plate 301, a spacer 311 which partially covers the conductive films 302 and a channel trench with a constant width is formed thereof, a reactive film 303 which can react with a sample, and a cover 306 with an opening 313 thereof.

The base plate 301 is preferred to be flat and straight. And the material of the base plate 301 is preferred to be electrical insulating and heat-resistant up to 60° C., hence the conductive film 302 and the reactive film 303 can be heated to dry thereon. The preferred base plate 301 can be made of, for example, PC plate, polyvinylchloride (PVC) plate, polyethylene terephthalate (PET) plate, glass fiber plate (FR-4), Bakelite ceramics, ceramic plate (CEM-1), glass plate or polyester sulfone plate.

Conductive films 302 comprise at least an isolated cathode part and an isolated anode part. Cathode part is partially covered by the spacer 311, and the two exposed ends individually are a cathode lead 307 and a reference electrode 309. Anode part is also partially covered by the spacer 311, and the two exposed ends are individually an anode lead 308 and a working electrode 310. The area of the working electrode 310 is larger than the reference electrode 309. The working electrode 310 and the reference electrode 309 are covered by reactive film 303, which can electrochemically react with a sample to induce an electrical effect. And the cathode lead 307 and the anode lead 308 individually connect to amperometric detector.

The spacer 311 partially covers on the conductive films 302 and the base plate 301. A strip of the spacer 311 is cut off to form a channel trench, which serves as a reactive region and is used to accommodate a sample here. The channel trench exposes the working electrode 310 and the reference electrode 309, and the reactive film 308 is formed in the channel trench to cover the reactive region. The thickness of the spacer 311 is preferred to be about 0.2 mm or above, hence the resistance of the sample covering the reactive film 303 can be reduced.

The reagent solution of the reactive film 303 contains an active species such as an enzyme, a protein or a chemical etc., which can undergo redox reactions and a mixed solution, which contains a polymer, an electron medium, a nonionic surfactant and a buffer solution.

The polymer of the reactive film 303 is used to fix the active species and the electron medium. About 1–4 wt % of polymer contributes to the reagent solution of the reactive film 303. The polymer can be chosen from PVP (Polyvinyl Pyrrolidone), PEG (Polyethylene Glycol), gelatin, dextran, PVA (polyvinyl alcohol), methylcellulose, carboxymethyl cellulose, albumin, chitin or a combination thereof.

The electron medium of the reactive film 303 plays a role of an electron acceptor or an electron donor in the electrochemical reaction between the active species and an analyte. The voltage, resistance or current variation of the electrochemical reaction can be transferred from the working electrode 310 and the reference electrode 309 through conductive film 302 to the anode lead 308 and the cathode lead 307, wherein the anode lead 308 and the cathode lead 307 connect to a detector. When the electrode test strip connects to a detector, the detector supplies a voltage to the electrode test strip by a voltage output device. The electrode test strip also connects to a receiver to receive the voltage, resistance or current variation of the above electrochemical reaction, and a display device converts the signal that receiver receives to the analyte concentration and display it. The electron medium is, for example, potassium ferricyanide. About 1–10 wt % of the electron medium contributes to the reagent solution of the reactive film 303.

Another component of the reactive film 303 is a nonionic surfactant, which disperses the active species to cover the hydrophobic reactive region. Less than about 0.3 wt % of the nonionic surfactant contributes to the reagent solution of the reactive film 303. The suitable nonionic surfactant comprises Triton X-100, lecithine, phosphatidyl choline, oleic acid, cyclodextrin and polyoxyethylene glycerine fatty acid ester.

The buffer solution of the reactive film 303 may be composed of, for example, citric acid, dipotassium phosphate, potassium phosphate, Tris or borate with deionized water. About 83.7–98 wt % of the buffer solution contributes to the reagent solution of the reactive film 303. The buffer solution is used to keep the optimum activity of the active species.

The cover 306 of the electrode test strip prevents the reactive film 303 from contaminating, and limits the sample volume in the reactive region. The opening 313 on the cover 306 is located above the reactive region and two holes 304 are located on the side of the electrode test strip. When one of the three holes 304 and 311 serves as the sample inlet, the other two serve as the gas outlets. This design can reduce the time needed for a sample to fulfill the reactive region to minimize the measurement errors and offer a more convenient way to operate this electrochemical electrode test strip of this invention.

Besides, a nitrate fiber film 312 can be used to cover the channel trench. The nitrate fiber film 312 is attached to the bottom surface of the cover 306 and its thickness is less than 0.15 mm. The nitrate fiber film 312 is optional. If the channel trench is covered with the nitrate fiber film 312, the time for a sample completely covering the reactive film 303 can be largely reduced, since the nitrate fiber film 312 is hydrophilic.

II. The Method of Preparing the Electrochemical Electrode Test Strip of This Invention This invention provides a manufacture method of a electrochemical electrode test strip, comprises the following steps:

(a) Conductive films cover an insulating base plate to form two separate electrodes, one serves as a cathode, and the other serves as an anode.

(b) An insulating spacer partially covers the conductive films to expose the first end of each electrode, and a channel trench with a constant width is formed in the spacer to expose the second end of each electrode. The first end of the anode serves as an anode lead, and the second end of the anode serves as a working electrode. Similarly, the first end of the cathode serves as a cathode lead, and the second end of the cathode serves as a reference electrode.

(c) A reactive film is coated on the reactive region in the channel trench by a one-step procedure. The reactive film is composed of an active species and a mixed solution, wherein the mixed solution comprises a polymer, an electron medium, a nonionic surfactant and a buffer solution.

(d) A nitrate fiber film covers on the channel trench.

(e) A cover with an opening, which exposes the reactive region, covers the insulating base plate.

Figure 4A:
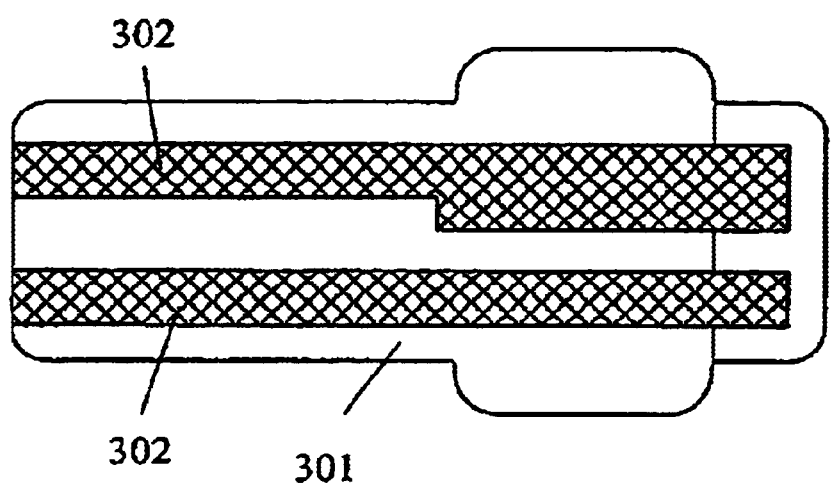
FIGS. 4A–4D are the progression of manufacturing steps in forming the above electrochemical electrode test strip according to one preferred embodiment of this invention.

In step (a) and FIG. 4A, a halftone is used to print out a layer of conductive films 302, which individually are a cathode and an anode on one surface of the base plate 301. Then a drying step is performed under a temperature of about 60 to about 80° C. The material of the conductive film 302 is preferred to be one of carbon glue, silver glue, gold glue, carbon-silver glue, cooper glue, carbon-platinum glue, or a combination thereof, which are suitable for halftone printing. For example, a combination of materials described above may be a silver-glue printed first and a carbon-glue printed next.

Figure 4B:
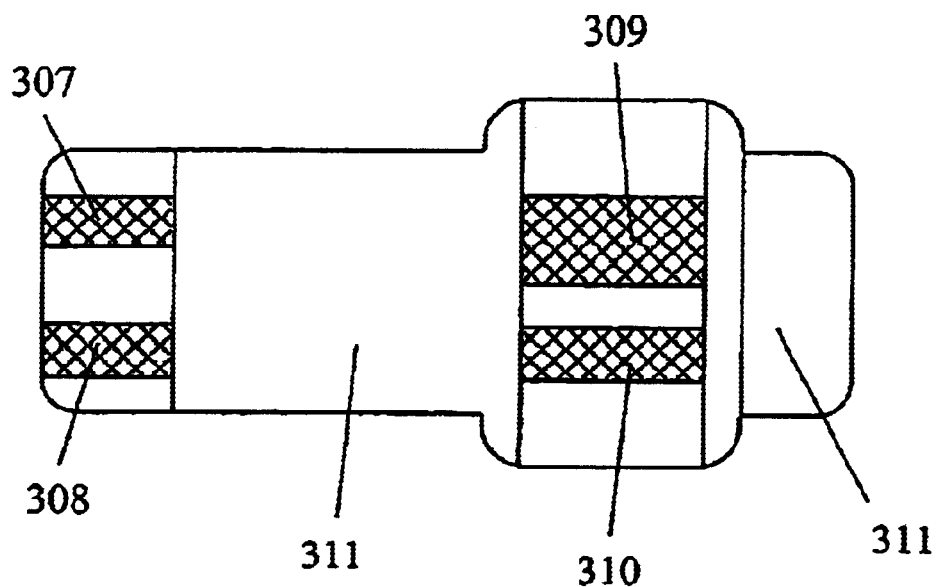

In step (b) and FIG. 4B, the insulating spacer 311, of which thickness is about 0.2 mm or above to reduce the resistance of the sample covering the reactive film 303, covers the conductive films 302. The channel trench of the insulating spacer 311 exposes one end of each electrode serves as a working electrode 310 and a reference electrode 309. The other exposed end of each electrode serves as a cathode lead 307 and an anode lead 308. The reactive region is in the channel trench.

In the step (c) and FIG. 4B, the reagent of the reactive film 303 is spread on the reactive region of the channel trench than dried to form the reactive film 303. The reagent solution of the reactive film 303 contains an active species, which can undergo redox reactions, and a mixed solution, which contains a polymer, an electron medium, a nonionic surfactant and a buffer solution. A feature of this invention is the reagent solution of the reactive film 303 is a single mixed solution. Therefore, only one procedure is needed to form the reactive film 303. There is no need to coat each component of the reactive region in multi steps. Hence the process of the electrochemical electrode test strip is easy to control and is suitable for mass-production to reduce the cost needed.

Figure 4C:
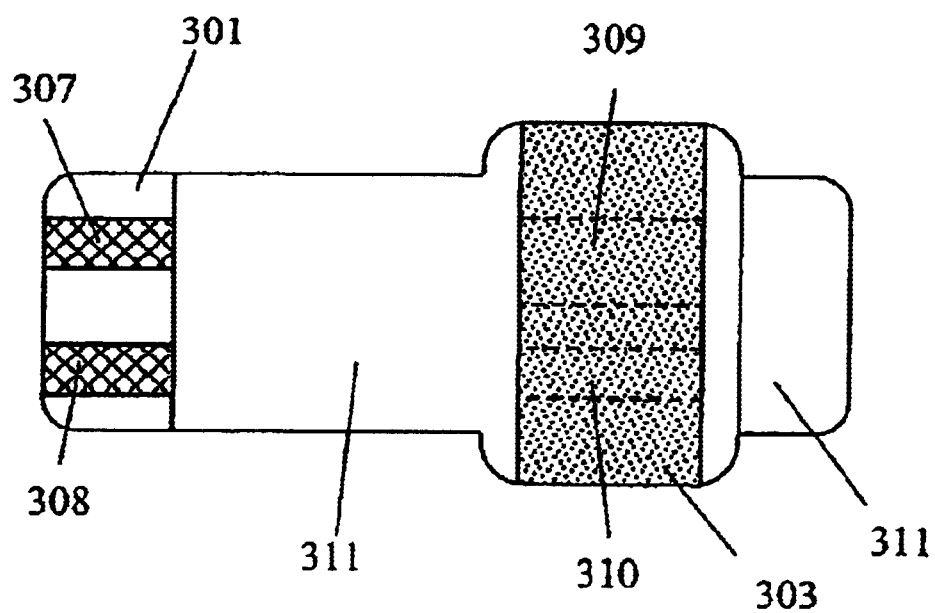

In step (d) and FIG. 4C, the channel trench is covered with a nitrate fiber film 312 to protect the reactive film 303. The nitrate fiber film 312 is less than 0.15 mm. The nitrate fiber film 312 is hydrophilic to shorten the time for a sample completely covering the reactive film 303.

Figure 4D:
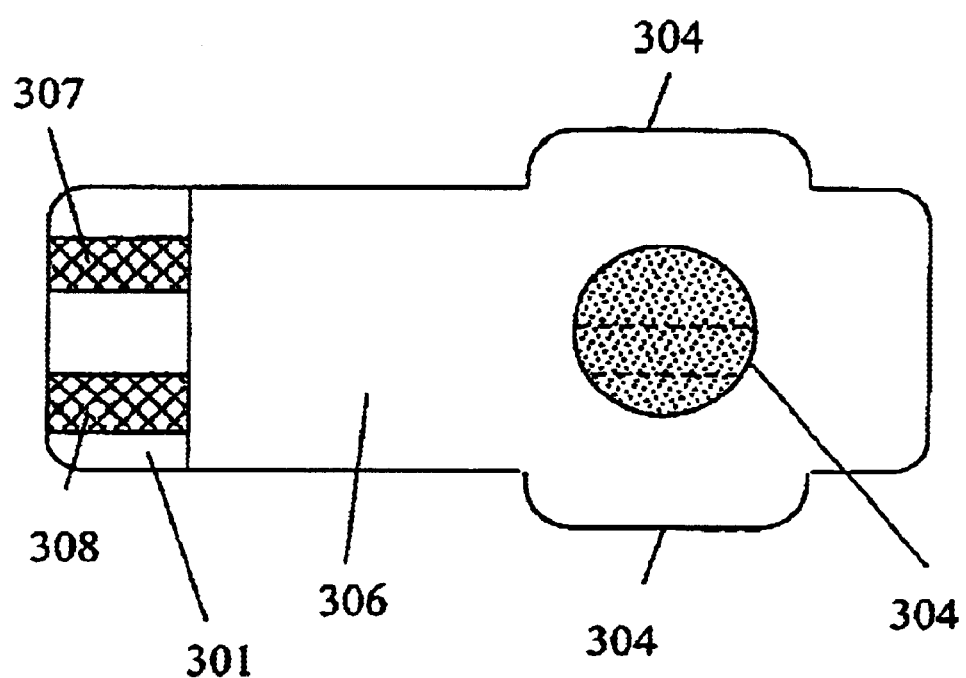

In step (e) and FIG. 4D, a cover 306 with an opening 304, which exposes the reactive region, covers the insulating base plate 301. Besides, two openings 304, which are surrounded by the cover 306, spacer 311 and the base plate 301, are formed simultaneously on the two ends of the channel trench.

For providing a further understanding of the invention, several embodiments are described below.

Embodiment 1: An Electrode Test Strip for Glucose Analysis

A halftone is used to print out two separate carbon-glue electrodes (i.e. conductive films 302) on a base plate 301, which is made of insulating PC. The two electrodes serve as a cathode and an anode individually. A drying step is performed under a temperature about 60 to about 80° C. to dry the carbon-glue. An insulating spacer 311 covers on the conductive film 302 next. The spacer 311 is used to form a reactive region, which is defined by a channel trench in the spacer 311 with a constant width. The exposed ends of the two electrodes serve as a cathode lead 307, an anode lead 308, a reference electrode 309 and a working electrode 310, individually.

A reagent solution is used to form a reactive film 303 on the reactive region by a drop-wise addition way. The compositions of this reagent solution are as follows:

| | |
|---|---|
| Glucose oxidase (270 U/mg) | 0.7 wt % |
| Carboxymethyl cellulose | 3 wt % |
| Potassium ferricyanide | 7 wt % |
| Triton X-100 | 0.08 wt % |
| Phosphate buffer (pH = 5.5; 0.1 M) | 89.22 wt % |

Then the reagent solution is dried under a temperature about 45° C. Then a nitrate fiber film 312 covers on the channel trench. Next, the cover 306 with an opening 313 is put on the spacer 311 to finish manufacturing the electrochemical electrode test strip, and the opening 313 is on the channel trench.

Figure 5:
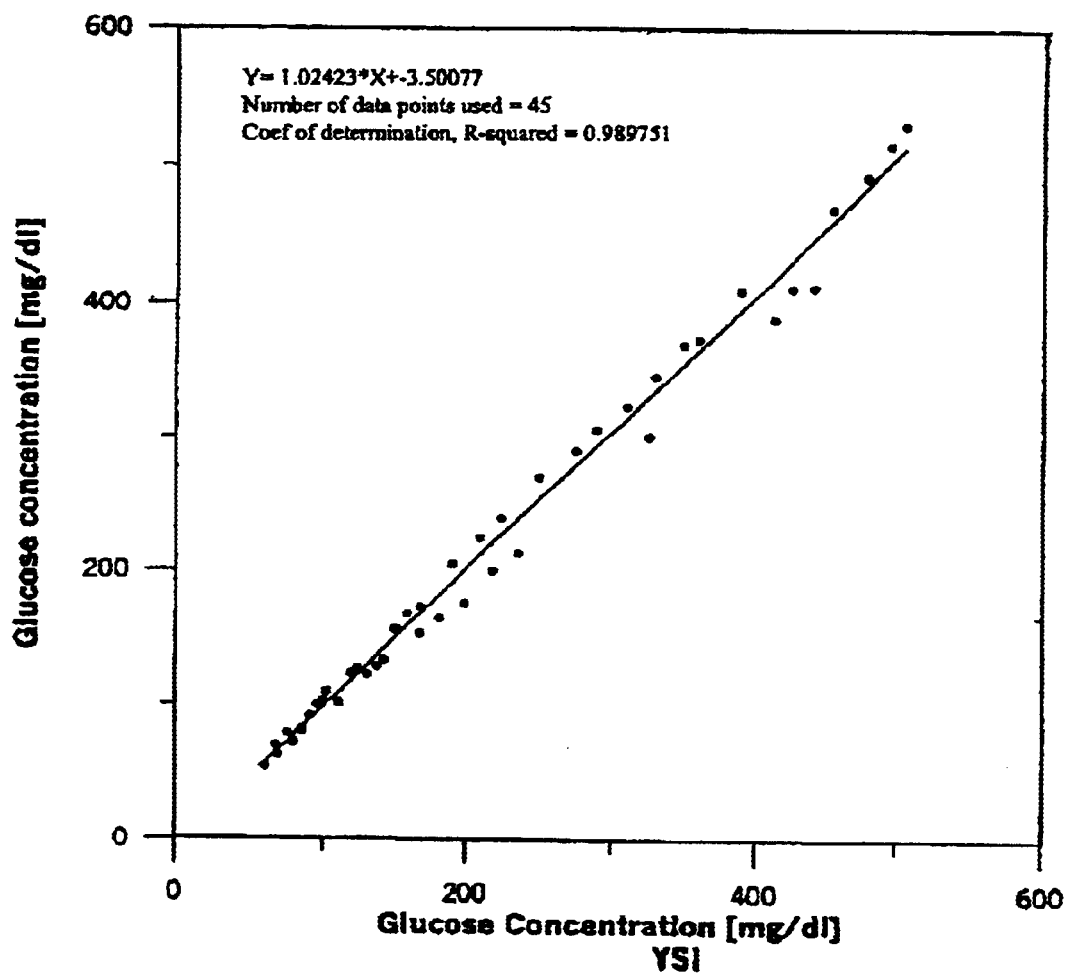
FIG. 5 is the comparison results between this invention and a bio-analyzer YSI 2300 (Yellow Springs Instrument Co. Model 2300).

The electrochemical electrode test strip described above is tested to detect the glucose concentration of a blood sample. The result obtained is the same with the result of a biochemical instrument YSI 2300 as shown in FIG. 5.

Embodiment 2: An Electrode Test Strip for Glucose Analysis

Repeat the steps performed in embodiment 1, but the compositions of this reagent solution are changed as follows:

| | |
|---|---|
| Glucose oxidase (270 U/mg) | 0.6 wt % |
| Albumin | 1 wt % |
| Methyl cellulose | 2 wt % |
| Potassium ferricyanide | 6 wt % |
| Triton X-100 | 0.09 wt % |
| Phosphate buffer (pH = 5.5; 0.1 M) | 90.31 wt % |

Embodiment 3: An Electrode Test Strip for Uric Acid Analysis

Repeat the steps performed in embodiment 1, but the compositions of this reagent solution are changed as follows:

| | |
|---|---|
| Uricase (1000 U/g) | 1.5 wt % |
| Methyl cellulose | 2.5 wt % |
| Citric acid solution (0.1 M) | 45 wt % |
| Triton X-100 | 0.1 wt % |
| Phosphate buffer (pH = 8.5; 0.2 M) | 89.41 wt % |

Embodiment 4: An Electrode Test Strip for Glucose Analysis

Repeat the steps performed in embodiment 1, but the compositions of this reagent solution are changed as follows:

| | |
|---|---|
| Glucose oxidase (270 U/mg) | 0.8 wt % |
| Gelatin | 2 wt % |
| Albumin | 0.5 wt % |
| Potassium ferricyanide | 7.5 wt % |
| Triton X-100 | 0.09 wt % |
| Phosphate buffer (pH = 5.5; 0.1 M) | 89.11 wt % |

Embodiment 5: An Electrode Test Strip for Glucose Analysis

Repeat the steps performed in embodiment 1, but the compositions of this reagent solution are changed as follows:

| | |
|---|---|
| Glucose oxidase (270 U/mg) | 0.66 wt % |
| Albumin | 0.5 wt % |
| Polyvinyl pyrrolidone | 2 wt % |
| Potassium ferricyanide | 7 wt % |
| Triton X-100 | 0.12 wt % |
| Phosphate buffer (pH = 5.5; 0.1 M) | 89.53 wt % |

From above description, the features of this invention are summarized as follows:

1. Since a sample is loaded from one of the three openings into the reactive region of the electrochemical electrode test strip. Therefore, the sample can be easily loaded into the reactive region in a much shorter time and the sample can easily cover the reactive film completely.

2. A redox reaction is subsequently occurred between an analyte of a sample and the active species. Since the sample can easily cover the reactive film completely to produce larger redox current an electrochemical instrument can easily detect the resulted current of the redox reaction and convert the signal to the analyte concentration. Therefore, the measurement errors can be largely reduced in this invention and the electrode test strip of this invention can be easily used in an electrochemical instrument.

3. The reagent solution of the reactive film is a single mixed solution. Hence the reagent solution can be spread on the reactive region and dried in one time. This will save much time and cost needed for manufacturing the electrode test strip.

4. The electrode test strip of this invention is disposable. Hence, there is no cross contamination between different samples. This is especially important for this electrode test strip used in hospital.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What claimed is:

1. A method of manufacturing a electrode test strip, comprising the steps of:
    offering an insulating base plate;
    printing a layer of conductive films to be a cathode and an anode, e cathode and the anode are isolated;
    forming a first spacer and a second spacer on the conductive films to expose two ends of the cathode and the anode, wherein a channel trench is formed between the first and the second spacer;
    spreading a reagent solution on a bottom surface of the channel trench;
    drying the reagent solution to form a reactive film in the channel trench; and
    forming a cover with a first opening on the spacer, wherein the first opening is located on the channel trench and two second openings are surrounded by the insulating base plate, the first spacer, the second spacer and the cover.

2. The method of the claim 1, wherein the reagent solution comprises an active species, a polymer, an electron medium, a nonionic surfactant and a buffer solution.

3. The method of the claim 1, wherein the polymer is about 1–4 wt % of the reagent solution.

4. The method of the claim 2, wherein the polymer is selected from the group consisting of Polyvinyl Pyrrolidone, Polyethylene Glycol, gelatin, dextran, polyvinyl alcohol, methylcellulose, carboxymethyl cellulose, albumin, chitin and a combination thereof.

5. The method of the claim 2, wherein the electron medium is about 1–10 wt % of the reagent solution.

6. The method of the claim 2, wherein the electro medium includes potassium ferricyanide.

7. The method of the claim 2, wherein the nonionic surfactant is less than about 0.3 wt % of the reagent solution.

8. The method of the claim 2, wherein the nonionic surfactant is selected from the group consisting of Triton X-100, lecithine, phosphatidyl choline, oleic acid, cyclodextrin and polyoxyethylene glycerine fatty acid ester.

9. The method of the claim 2, wherein the buffer solution is about 83.7–98 wt % of the reagent solution.

10. The method of the claim 2, wherein the buffer reagent of the buffer solution is a selected from the group consisting of citric acid, dipotassium phosphate, potassium phosphate, Tris and borate.

11. The method of the claim 2, wherein between the steps of drying the reagent solution and forming a cover further comprises a step of covering a nitrate fiber film on the channel trench.

* * * * *